United States Patent [19]

Blake et al.

[11] Patent Number: 5,316,730
[45] Date of Patent: May 31, 1994

[54] DISPOSABLE CARTRIDGE FOR INVESTIGATING PHYSICAL PROPERTIES OF BLOOD

[75] Inventors: Joseph W. Blake, Norwalk, Conn.; Robert Cousineau, Hartsdale, N.Y.; Mark Rosen, Hackensack, N.J.; William Watson, Greenwich, Conn.

[73] Assignee: XYLUM Corporation, Scarsdale, N.Y.

[21] Appl. No.: 987,469

[22] Filed: Dec. 7, 1992

[51] Int. Cl.$^5$ .................... G01N 11/04; G01N 11/08; G01N 33/49
[52] U.S. Cl. ...................................... 422/73; 128/638; 422/82.05; 422/82.13; 436/69; 436/70
[58] Field of Search ................ 422/73, 82.05, 82.13; 73/64.1; 128/638; 436/69, 70

[56] References Cited

U.S. PATENT DOCUMENTS 5,047,211  9/1991  Sloane et al. ................. 422/73

FOREIGN PATENT DOCUMENTS 0129425  12/1984  European Pat. Off.

Primary Examiner—Jill A. Johnston
Attorney, Agent, or Firm—Pollock, Vande Sande & Priddy

[57] ABSTRACT

A disposable cartridge for measuring the physical properties of blood is disclosed. A waste compartment supports a platform having first and second syringe fittings. First and second syringes containing blood samples to be measured are positioned within the fittings. At least one testing station is located on the platform for subjecting blood flowing from one of the syringes to a test station, and the testing station is connected at a second end to the waste compartment. Tests on blood running through each of the blood channels may be conducted by inducing various platelet activation conditions, such as piercing a channel, or putting a platelet activating substance within a test channel. The cartridge interfaces with a test stand which will measure pressure changes within each of the test channels.

19 Claims, 4 Drawing Sheets

DISPOSABLE CARTRIDGE FOR INVESTIGATING PHYSICAL PROPERTIES OF BLOOD

The present invention relates to disposable devices for making measurements of the physical properties of blood. Specifically, a cartridge has been designed which is especially useful in conducting experiments on native, non-anticoagulated blood.

In the treatment of various blood disorders, it has been necessary to make measurements on whole, native blood to assess the formation of platelets and the adequacy of haemostatic functions of the blood before embarking on specific medical procedures for patients having these disorders. Further, other disorders such as myocardial infarction, stroke, thrombolysis or blood dissolution properties, must be monitored and assessed repeatedly following recovery to prevent recurrence of a blood clot.

Techniques for measuring the physical attributes of platelet activation, all of which is related to the foregoing disorders, have been the subject of numerous investigations. The difficulty in making such measurements lies in the difficulty to collect native whole blood which has not been anticoagulated and conduct experiments which do not induce any platelet activation except under very controlled circumstances. In investigating the behavior of native whole blood, a device for performing in vitro haemostasis on native whole blood, is described in EPO Application No. 129425. This patent describes a laboratory technique which is capable of simulating bleeding. A fresh supply of native blood is connected to a polyethylene tube. A flow of blood is started through the tube and bleeding is simulated by establishing a hole in the tubing of a known diameter. The bleeding which occurs through the hole is monitored, both optically and through a pressure measurement of the flow of blood.

A further improvement of this technique is described in a later International Patent Application PCT/GB87/00633, having an international filing date of Sep. 10, 1987. In this patent, multiple channels of blood flow were established, and concurrent measurements of haemostasis were made in each of the blood flow channels. This permitted a control channel having blood drawn at the same time, thus having substantially the same chemical composition to be measured and compared to each other.

The laboratory technique set forth in the above-referenced patent documents requires a fairly high level of skill on the part of the personnel conducting such tests. Further, as blood is known to carry viruses, including the deadly HIV virus, it is necessary that personnel always take precautions to avoid contact with the blood.

A disposable blood-handling cassette is described in U.S. Pat. No. 5,047,211 which will permit such tests to be carried on in accordance with the preceding patent documents, while isolating medical personnel from coming in contact with the blood under test. The device, which is completely self-contained, includes multiple reservoirs which receive a blood sample for carrying out the experiments and investigation of blood, as set forth in the previously identified patent documents.

Further investigation of these techniques have demonstrated how the handling of blood, even in a disposable cartridge can result in platelet activation before any testing begins. The process of extracting blood from a human donor in itself can activate platelets which interfere with the investigation of blood under controlled conditions.

It has also been found that further control over punching holes in a blood-carrying tubing is necessary in order to provide for repeatability between tests of succeeding samples of blood.

SUMMARY OF THE INVENTION

It is an object of this invention to provide for a disposable cartridge which can be used to carry out tests on blood.

It is a more specific object of this invention to provide for a disposable cassette which may be used in haemostasis and thrombolysis measurements, and which effectively isolates infected blood samples from users of these devices.

It is yet a more specific object of this invention to provide a device which is designed to avoid inadvertent platelet activation in a sample of blood under test.

These and other objects of the invention are provided by a disposable cartridge which is capable of conducting tests on whole blood. The cartridge is designed to introduce a minimum amount of disturbance to the blood's physical properties, and specifically to avoid platelet activation through handling of the blood samples. The cartridge creates an in vitro environment which models the circulatory system with regard to temperature and flow. In doing so, shear force experienced by the blood is accurately controlled. In this way, platelet activation is maintained under control until tests are performed on the blood. The device therefore permits the simulation of normal circulatory blood conditions, as well as simulating a disease environment or injury during testing.

In carrying out the invention, the disposable cartridge incorporates a totally isolated compartment for tested blood which will preclude any inadvertent contact with medical personnel. The compartment supports a platform which includes at least one receptacle for receiving a blood sample vessel such as a syringe. The use of the syringe as the blood vessel avoids the platelet activation which occurs when transferring the blood from a syringe used to draw the blood from the human donor to a reservoir in another test device. Further, the syringe which acts as a blood sample vessel is exposed to a heating plate of a test stand for maintaining the blood sample vessel at a constant temperature, which improves the control over experiments being conducted.

In accordance with the preferred embodiment of the invention, experiments are conducted with two blood samples contained in two syringes. The first blood sample is used in a test channel to simulate bleeding. The second blood sample is used in a second test channel to simulate the effect of a platelet-activating substance contained in the test channel of the two-channel device on blood flowing through the test channel.

The first of the channels provides for a flow of blood through a punching station, which forms an accurately-defined opening in the blood tube to simulate bleeding. A pressure chamber is provided which contains a volume of immiscible fluid. Blood exiting the test channel enters its own pressure chamber where it displaces the volume of immiscible fluid through an orifice into a waste compartment. A test stand associated with the disposable cartridge, provides a fluidic connection between the pressure chamber and a pressure transducer.

As blood flows through the test channel, the immiscible fluid is displaced through an orifice generating pressure within the pressure chamber. Changes in measured pressure will provide an accurate monitoring of platelet activity. In accordance with the preferred embodiment of the invention, the bleeding chamber is filled with a saline solution. Drops of blood exiting the punctured opening in the channel having a punching station can be observed in the tapered end of the bleeding chamber via an optical detecting device.

The second test channel provides for a second flow of blood from a second syringe past a platelet-activating substance, into a second pressure chamber. The second pressure chamber includes a volume of immiscible fluid which is displaced through orifice into the waste compartment. A second transducer measures the changes in pressure within the pressure chamber as a measure of the platelet activity.

DESCRIPTION OF THE PREFERRED EMBODIMENT

Figure 1:
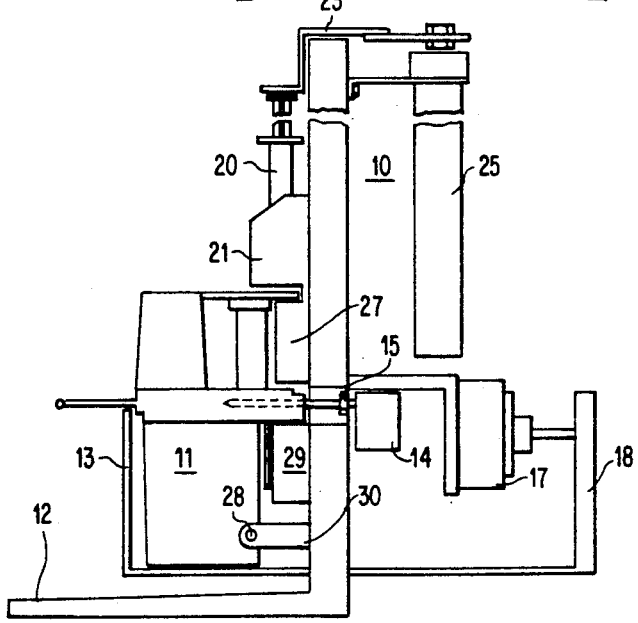
FIG. 1 illustrates a test stand having a disposable cartridge in accordance with the preferred embodiment of the invention for measuring the physical properties of blood.

Referring now to FIG. 1, there is shown a disposable cartridge 11 in accordance with a preferred embodiment of the invention, which is received within a test stand 10. The cartridge 11 supports a pair of syringes 20, which contains native, non-anticoagulated blood obtained from a donor. The cartridge 11 will provide for a two-channel test device for measuring the properties of blood flowing from each of the syringes 20 into first and second test channels which terminate in a waste compartment. The cartridge 11 is completely disposable and includes two fittings for receiving each of the ends of syringes 20. The assembly of the cartridge 11 and syringes 20, having two samples of blood from which measurements of certain physical conditions of the blood are to be made, are inserted into the test stand 10 during the performance of tests on the samples of blood.

The test stand 10 includes a support 13 which is used to position the cartridge 11 with respect to the test stand 10. The support 13 is driven by a stepping motor 17 to move the cartridge 11 against the heaters 21 and 29 of the test stand 10.

The test stand 10 supports two heaters 21 and 29. Heater 1 will maintain each of the syringes 20 at a preferred temperature to keep test conditions constant for all blood samples being measured. The second heater 29 will maintain the two test channels of the cartridge 11 carrying the blood under test substantially equal to that of the syringes 20.

The cartridge 11 is arranged in accordance with the principles set forth in the aforesaid patent documents so that an immiscible displacing fluid is introduced into the syringes 20, displacing the blood through the test channels. The displacing immiscible fluid is supplied from a pair of reservoirs which are pressurized with air and received through sealed coupling in the cartridge 11. Another pair of sealed couplings are connected to a pair of conduits for supplying a displacing fluid from another reservoir to each pressure chamber which terminates the two blood channels. Following filling of the pressure chambers with immiscible fluid, a pair of pressure transducers connected to the pair of conduits monitor pressure changes in each blood channel. Changes in flow due to test conditions in each channel result in a pressure change which can be accurately monitored.

The plungers on the syringes 20 are maintained in position during pressurization of the syringes 20 with the immiscible fluid by a retainer 23 which is connected to a linear actuator 25. Control over linear actuator 25 will lower the retainer 23 to maintain the plungers of each of the syringes 20 in their unpressurized position. As the size of the blood sample may change, it is necessary to have the retainer 23 adjustable to accommodate different plunger heights.

In accordance with the principles set forth in the devices and processes described in the aforesaid patent documents, a support 30, supporting an optical detector 28, is also provided. The optical detector 28 detects blood which flows in a bleeding chamber during a test conducted in one of the blood channels.

Figure 2:
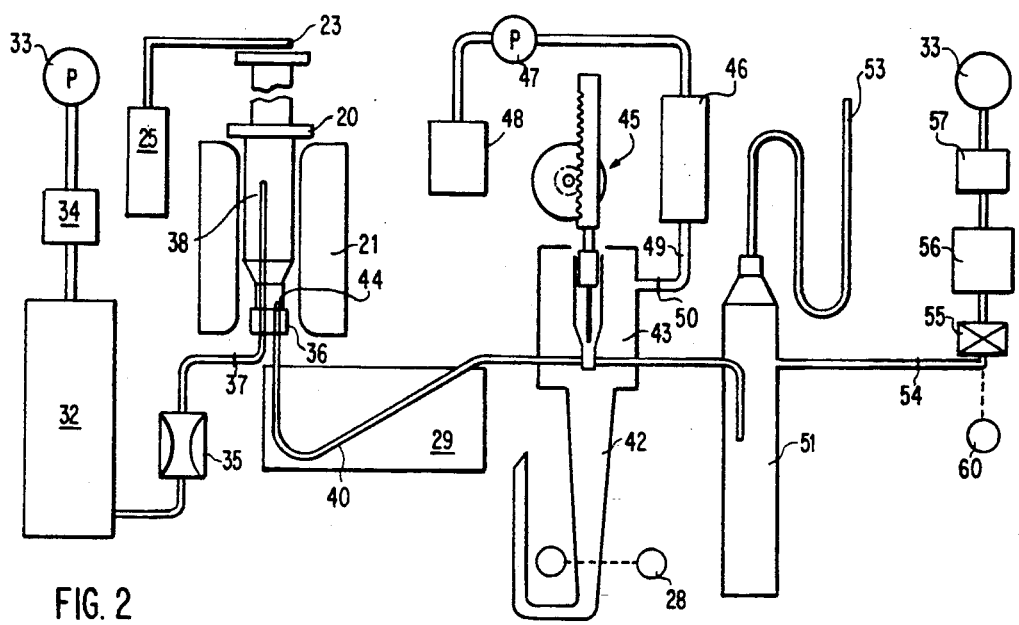
FIG. 2 illustrates a fluidic diagram of the first test channel provided by the cartridge and test stand of FIG. 1.
Figure 3:
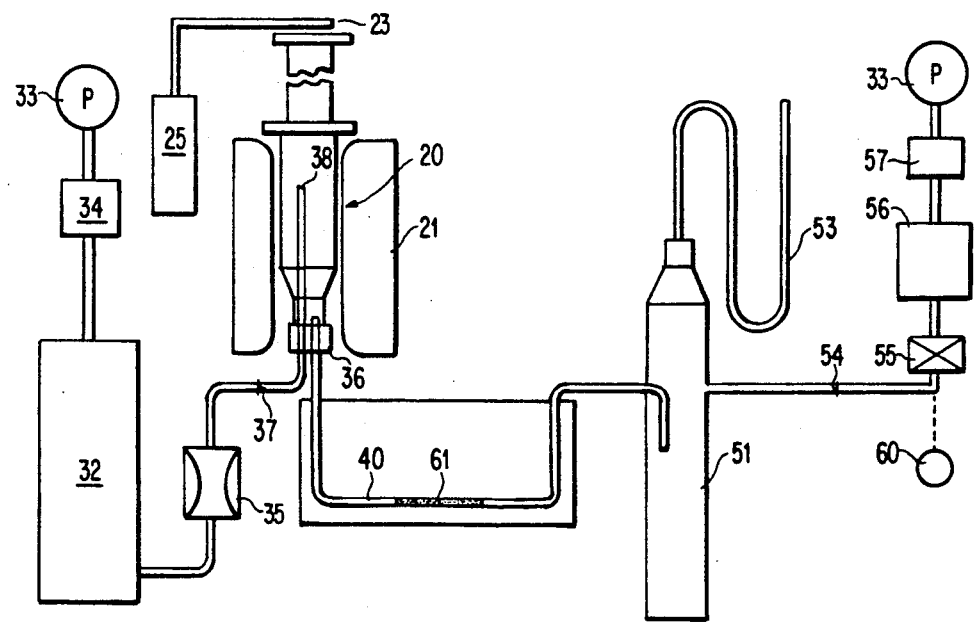
FIG. 3 is a fluidic diagram of a second test channel provided in the disposable cartridge and test stand arrangement of FIG. 1.

The two test channels which are provided by the system of FIG. 1, are schematically illustrated in FIGS. 2 and 3. FIGS. 2 and 3 illustrate the fluid circuits which are provided by each of the test channels in the cartridge device. FIG. 2 illustrates a test channel wherein the process of platelet activation is monitored by puncturing a blood-carrying channel 40 with a punching needle assembly 43. The punching needle assembly 43 includes a guide and needle which, when driven by the linear actuator 45, will pierce a pair of precisely-positioned holes across a common diameter in the blood carrying channel 40, at a controlled rate.

The blood-carrying channel 40 is connected to the receptacle 36 for receiving the end of the syringe 20. The receptacle 36 also includes a standpipe section 38 which is connected to receive, through the sealed coupling member 37, a supply of immiscible displacing fluid.

The blood channel 40 terminates in a pressure chamber 51. The pressure chamber 51 also receives a volume of immiscible displacing fluid from a second sealed coupling member 54, connected to another source of displacing fluid.

Initialization of the test channel requires that air pressure from pump 33 be forced through air regulators 34 and 57 to a pair of oil supplies 32 and 56.

The pressure chamber 51 is filled and air expelled via an orifice as the oil supply enters from valve 55 through the sealed coupling member 54 of the cartridge. The orifice is provided by the tube 53 which is connected at one end to the domed pressure chamber 51 and at the other end to the waste compartment 63.

As the volume of immiscible fluid is filling the pressure chamber 51, a similar column of displacing fluid is entering through the flow regulator 35 and cartridge sealed coupling member 37. The standpipe 38 is connected through the receptacle 36 to the sealed coupling member 37, and permits the immiscible oil to enter the syringe. The oil displaces the blood through the proximal end 44 of blood channel 40.

Blood which flows through the channel 40 displaces the volume of immiscible fluid contained in the pressure chamber 51 through the orifice established by the tube 53, and into the waste compartment 63. The flow of blood thus established from the syringe 20 through channel 40 represents an in vitro normal circulatory condition for the blood. Platelet activation is minimized until the punching operation commences which will simulate bleeding, resulting in a state of high shear rate causing platelet activation.

Prior to operating the linear actuator 45 which drives the punching mechanism 43, a saline solution is pumped from a supply 48, via pump 47, through a coupling 50 into the bleeding chamber 42. The saline solution which is heated in heater 46 fills the tapered portion of bleeding chamber 42 and washes the exiting blood from the hole punched in the blood-carrying channel 40. Care is taken to maintain and regulate the temperature of the saline solution constant.

The tapered portion of the bleeding chamber 42 is observable by the optical detectors 28. As is set forth in the foregoing patent documents, the duration of bleeding is detected by optical detector 28.

Once the pressure chamber 51 has been filled with the volume of immiscible fluid, the valve 55 is closed, isolating the source of immiscible fluid from the pressure chamber 51, leaving coupling member 54 pressure transducer 0 connected to the pressure chamber 51. The pressure in this hydraulic circuit formed from the syringe 20, blood-carrying channel 40 and pressure chamber 51 will be monitored and various changes in the physical characteristics of blood can be monitored by the pressure transducer 60. Chief among these changes includes platelet aggregation which results from shear forces on the blood exiting the punched hole in the channel 40. Initially, blood exiting the holes will be detected in a lowering of the pressure monitored by pressure transducer 60. Further, an optical signal will be produced as blood flows into the bleeding chamber 42. As the platelets aggregate in the hole, the resulting pressure changes will be monitored by the transducer 60. This change in pressure occurring during the punching of the holes, as well as the subsequent coagulation which occurs in the lumen of the tubes, will give the clinician significant data regarding the condition of the blood under test.

The second channel provided by the disposable cartridge is shown in FIG. 3. Identical components for this second test channel are marked with the identical reference numerals. The test channel of FIG. 3 does not include a punching station for piercing the blood-carrying tube 40. This channel can suffice as a control channel and pressure changes noted by the transducer 60 are accurately compared with the pressure transducer 60 of FIG. 2.

Additionally, a platelet-inducing substance 61 may be introduced into the channel 40 of FIG. 3, and the downstream pressure measured via the pressure transducer 60. This platelet-forming substance 61 may be a collagen substance, as described more particularly in the aforesaid international patent application. Platelet activation occurring from the substance 61 will result in a change in pressure for the test channel. These events may be accurately monitored by the pressure transducer 60, giving the clinician an opportunity to compare pressure changes for different samples of blood in different tests. The second test channel can also provide information to interpret the data obtained from the first channel. The initialization of the test channel is the same as that of FIG. 2, wherein the pressure chamber 51 receives a volume of immiscible fluid, while the syringe 20 receives, through standpipe 38, a similar volume of immiscible fluid.

In both devices, the outlet tubes 53 for the pressure chambers are connected to the waste compartment and displaced immiscible fluid enters the waste compartment and is securely maintained within the cartridge. The displacement of the immiscible fluid through the orifice created by the outlet tubes 53 creates a pressure which is monitored by the pressure transducer 60. Thus, flow conditions are accurately monitored as long as the flow through the orifice continues. It should be noted that the punched holes in tube 40 of the first channel will reduce the flow into pressure chamber 51, dropping the monitored pressure. When the blood totally clots, pressure drops to zero since there is no flow. The optical monitoring provided by optical detector 28 will detect any expulsion of a platelet plug from the punched holes. At the conclusion of the tests, the entire cartridge with connected syringes may be disposed of safely.

Having generally described the tests carried out by the test stand 10 and disposable cartridge 11, a more detailed description of the disposable cartridge will now be made.

Figure 4:
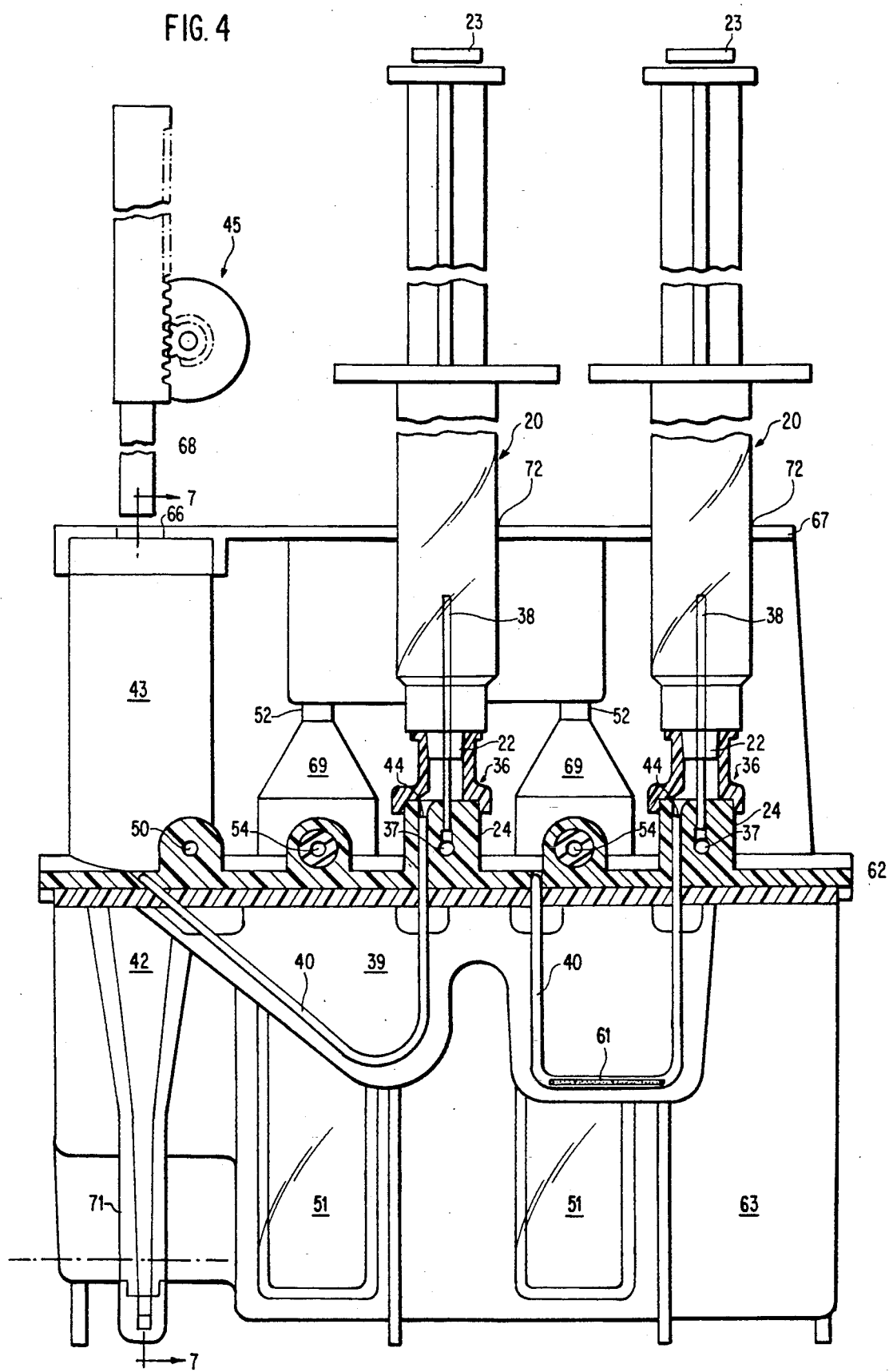
FIG. 4 is a first section view of the cartridge inserted in the test stand.

Referring now to FIG. 4, there is shown a partial section view of the cartridge 11, as viewed from the test stand which receives the cartridge 11. The cartridge 11 includes a waste compartment 63 supporting on the top surface thereof a platform 62. Those components shown in FIG. 4 can be made of a plastic material through injection molding or similar processes.

The platform 62 supports a pair of studs 24, each of which receives the flared ends of the syringe receptacles 36. The studs 24 support the standpipes 38 which are coaxial with the axis of the receptacles 36. The end of the receptacles 36 which receives the front tip 22 of each of the syringes 20 has a luer fitting taper to provide a force fit, tight against any blood or pressurizing fluid leakage.

The stud 24 for each of the test channels includes a fluidic coupling member 37, which may be an elastomeric substance which is pierced by an injection needle or pointed cannula from the test stand 10. Displacing fluid is received through the coupling member 37 and supplies the immiscible displacing fluid through the standpipes 38 into the body of the syringes 20.

Each of the pressure chambers 51 extends through the platform and have domed portions 69 which are connected to the outlet tubes 53 which provide an orifice. Displacing fluid for the pressure chambers 51 is received through the couplings 54, which also may be of an elastomeric insert, pierced by a needle or pointed cannula supplying the displacing fluid. A similar fluid coupling is provided at 50 for injecting a saline solution into the bleeding chamber 42.

Each of the blood-carrying tubes 40 for each test channel is supported on a surface 39. Surface 39 is positioned so that in use it touches the heater 29, thereby maintaining constant the temperature of the blood-carrying tubes 40. The receptacles 36 and studs 24 are also positioned such that each of the syringe bodies 20 is located within the heater 21.

The blood carrying tubes 40 have a routing path which is initially straight down, and then routed upward. A collagen substance 61 is shown introduced in one of the blood carrying tubes which is by the radius of the blood carrying tube.

A top cover 67 is fixed to the platform 64 and includes a pair of guide holes which support the syringes 20 in alignment with the receptacles 36. The cover 67 also includes a hole 66 which receives the ram 68. Ram 68 is advanced by the linear actuator 45 towards the punching mechanism 43 at a controlled speed to control the shape of the hole being formed.

Figure 5:
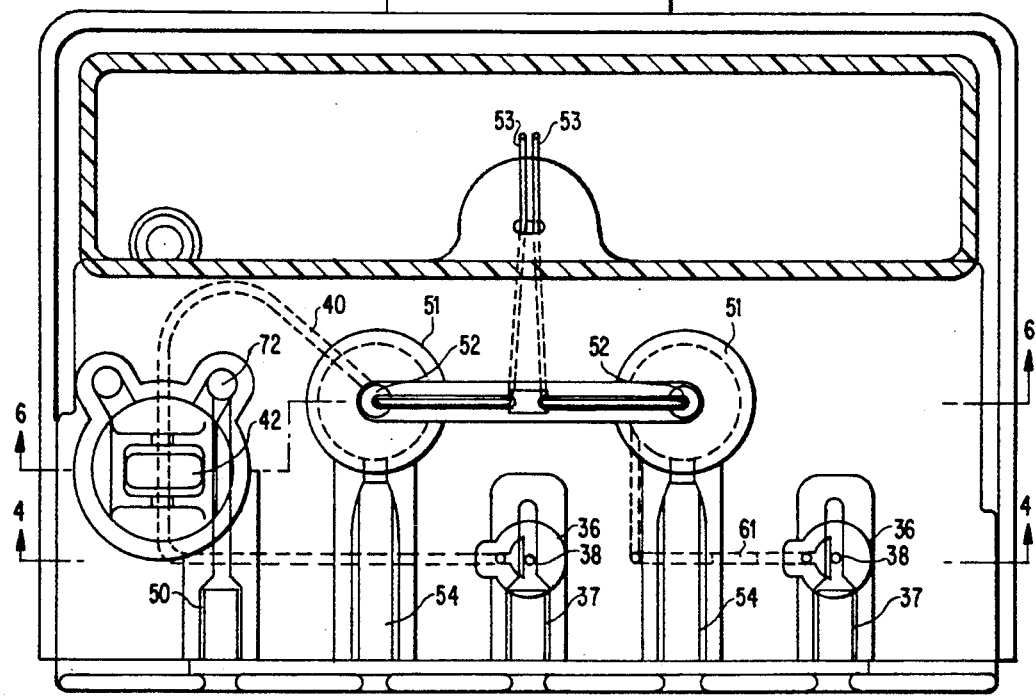
FIG. 5 is a top section view of the disposable cartridge of FIG. 4.

The section view of FIG. 5 illustrates the test channels. The test channels include the bleeding chamber 42, as well as the platelet-activating substance 61. Also shown is an outlet 72 for the saline solution which enters via the coupling 50 to fill the bleeding chamber 42.

Figure 6:
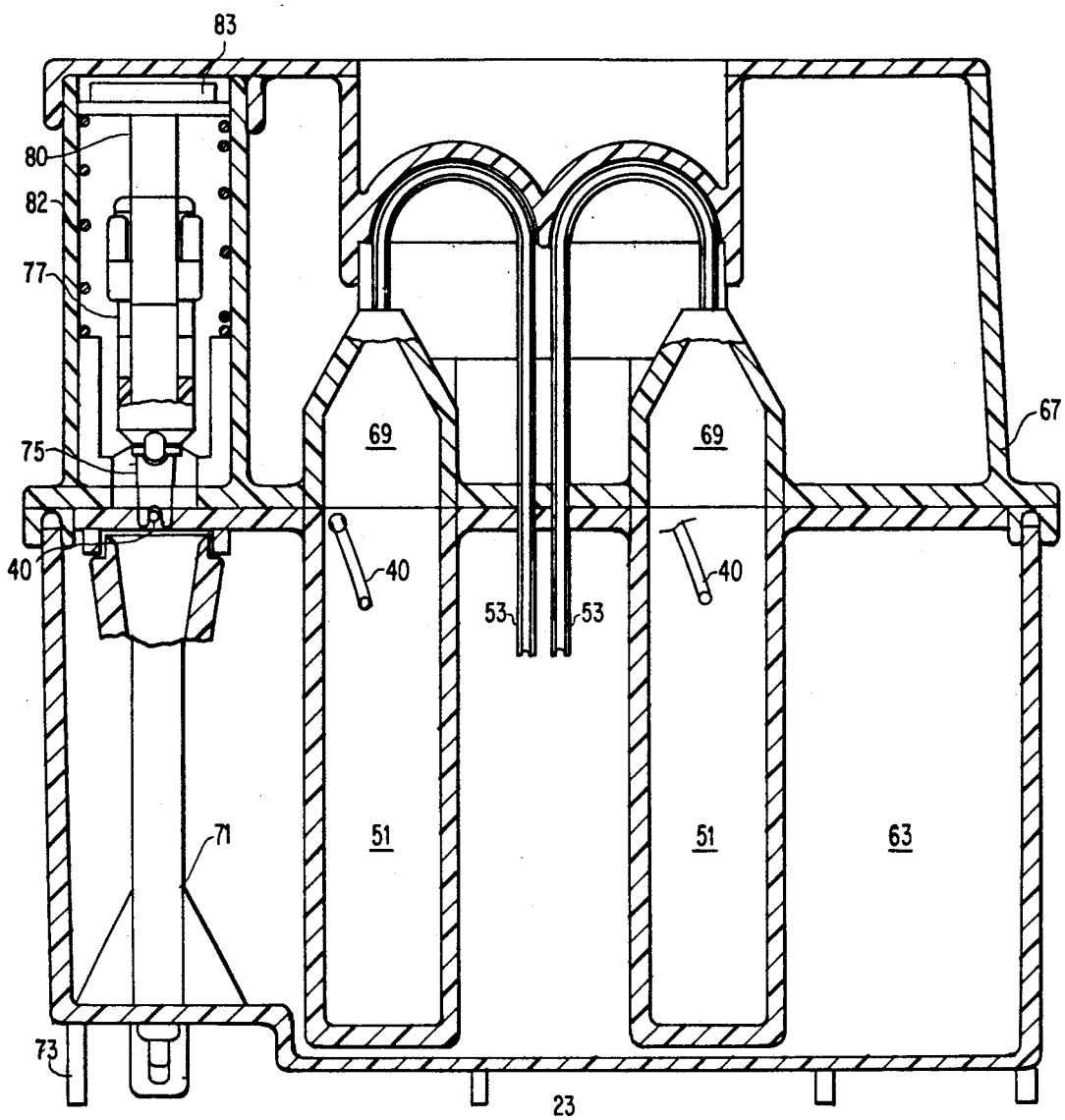
FIG. 6 illustrates a second, section view of the cartridge illustrating the pressure chambers which terminate each test channel.
Figure 7:
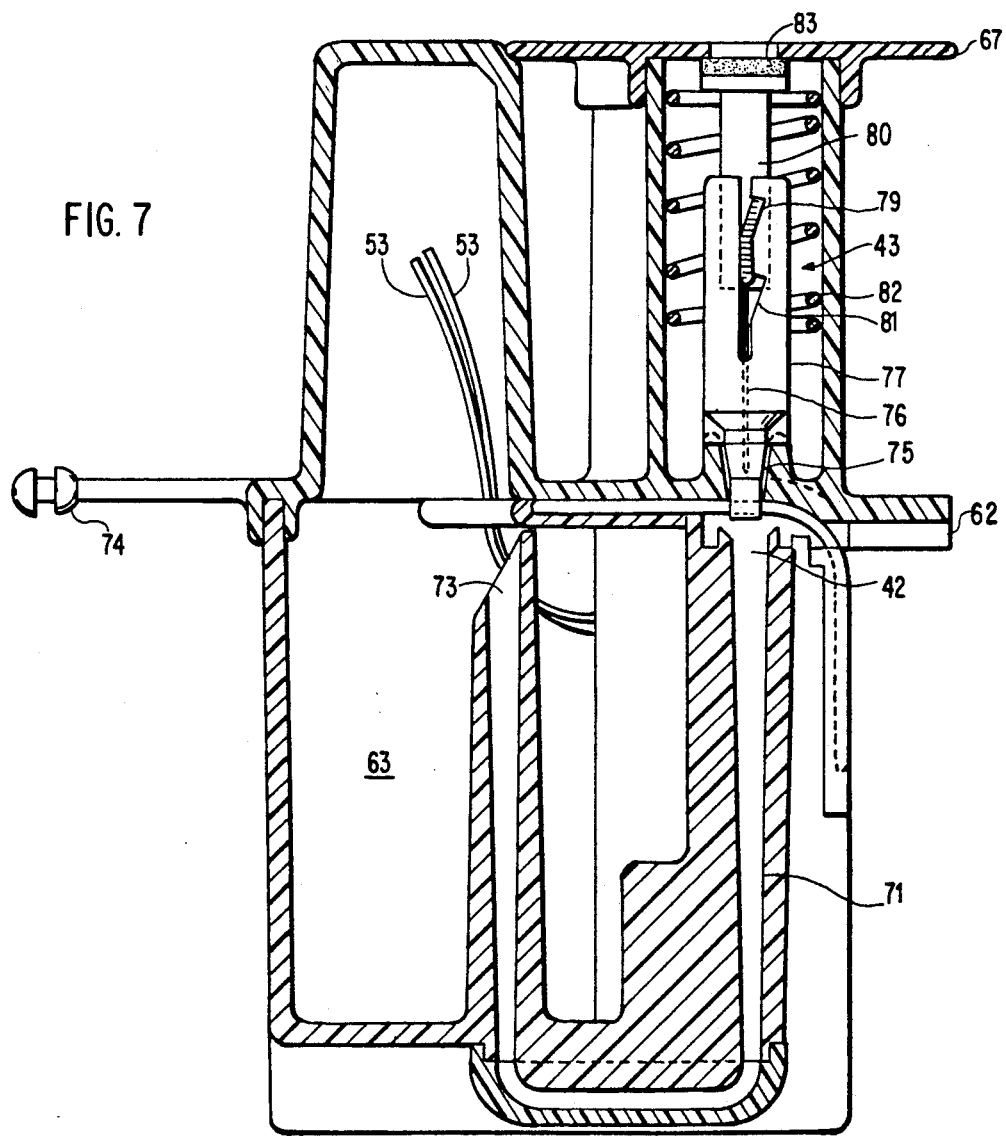
FIG. 7 illustrates another section view of the punching station which pierces a precise hole in one of the test channels.

Details of the cartridge punching station 43 are shown more particularly in FIGS. 6 and 7. The punching station includes a plunger 80 which slides within a sleeve 77. A guide 75 having a forked end positioned over the blood-carrying tube 40 is connected to the sleeve 77. A centrally-located needle 76 is connected to move with the plunger 80 when the ram 62 is accelerated against the surface 83. The end of the needle 76 is located within a through-hole in the forked end. The forked end positions the needle tip in line with the inner diameter of the blood-carrying tube 40.

The plunger 80 moves inside the sleeve 77, pushing the needle through the hole in the guide 75, and pierces opposite sides of the blood-carrying tube. A detent on the plunger 80 moves between a first notch 79 and second notch 81 in the sleeve 77. As the ram 82 pushes plunger 80 against the force of a spring 82 when the ram is retracted, the spring 82 withdraws the plunger 80, the needle 76 and guide 75. The result is a pair of holes in the blood-carrying tube 40, which permits bleeding to occur in the bleeding chamber 42. The elastomeric material 83 at the top of the plunger seals the cartridge against leakage.

The blood profusing from the hole drains via the tapered section 71 with the saline solution into the waste compartment 63, where it is captured. Other waste material from the pressure chambers 51 also exit via the drain tubes 53 to the waste compartment 63. The level of saline in the bleeding chamber 42 is controlled by the rate at which saline is introduced, and the height of the exit port 73. The level of saline is maintained at a level which insures washing of the holes punched in the blood-carrying tubes.

The foregoing structure of the cartridge provides for a minimum disturbance to blood samples which are to be tested under very controlled test conditions. By using the syringes as the reservoir, the inadvertent activation of platelets in the test sample are kept to a minimum. Further, the entire cartridge is designed such that the blood sample throughout the test channel can be maintained at a constant temperature, thus minimizing the effects of temperature differentials on each test being conducted. Once the test is completed, the motor 17 of FIG. 1 can be reversed and by grasping the handle 74 of the cartridge, the entire cartridge with connected syringes may be disposed of without risk of contamination to any of the testing personnel.

As the cartridge can be made from any suitable plastic material, the costs can be maintained at a minimum, while insuring safety to those carrying out such tests.

Thus, there has been described with respect to one embodiment, an example of the invention. Those skilled in the art will recognize yet other embodiments defined more particularly by the claims which follow.

What is claimed is:

1. A disposable cartridge for measuring the properties of blood comprising:
   a waste compartment for receiving blood samples which have been subject to measuring;
   a platform supported on said waste compartment including first and second fluidic couplings which receive the front tip of first and second syringes which contain blood samples, connecting said platform and syringes together, forming a leak-proof assembly, said fluidic couplings providing a pressurizing fluid to said syringes and having an outlet for delivering pressurized blood;
   guide means for supporting said syringes in alignment with said fluidic couplings;
   first and second blood-carrying tubes mounted along a routing path on a surface, connected to each of said outlets;
   a punching mechanism comprising:
   a ram operated punching needle, said needle being positioned during a punching operation by a guide to punch an opening in said first blood carrying tube, permitting blood to exit through said opening;
   a first domed chamber receiving the end of said first blood-carrying tube, and receiving a pressurizing fluid from a source of pressurizing fluid for displacing air through a restricted orifice, and for providing a pressure transducer connection which measures changes in blood pressure occurring during a flow of blood through said first blood-carrying tube into said first domed chamber, displacing pressurizing fluid through said restrictive orifice into said waste compartment; and
   a second domed chamber receiving the distal end of said second blood carrying tube, and receiving a pressurizing fluid for displacing air through a restricted orifice in said second domed chamber, as well as providing a connection to a pressure transducer for measuring changes in blood pressure in said second blood-carrying tube from blood flowing through said domed chamber displaying pressurizing fluid through said restrictive orifice into said waste compartment.

2. The disposable cartridge of claim 1 wherein said second blood-carrying tube contains a platelet-induced body.

3. The disposable cartridge of claim 1 further comprising a vertically extending conduit connected to said fluidic couplings which is received in said syringes, and supplies said pressurizing fluid to said syringes.

4. The disposable cartridges of claim 3 wherein said guide means position said syringes to be tangential to a rear edge of said cartridge so that said syringes can be located against a common heating surface.

5. The disposable cartridge of claim 1 further comprising a tapered chamber having an axis aligned with said punching needle, said chamber tapered to receive an optical sensor for detecting blood exiting from a punched hole in said first blood-carrying tube.

6. The disposable cartridge of claim 5 wherein said tapered chamber includes an inlet for receiving a saline solution which washes blood from said hole punched in said first blood-carrying tube.

7. The disposable cartridge of claim 1 each of said first and second blood-carrying tubes in a common plane to permit said tubes to be heated by a heating surface.

8. An apparatus for measuring the properties of blood comprising:

a disposable cartridge including first and second supports for vertically supporting two blood-filled syringes, in first and second fluidic couplings forming a sealed assembly therewith, said couplings having inlets for receiving a pressurized fluid, and outlets for supplying blood and first and second testing channels for carrying blood from said outlets, and a waste receptacle for receiving tested blood from said first and second testing channels; and, a test stand for receiving said cartridge, said test stand having a heater for maintaining said blood-filled syringes at a constant temperature, and including means for maintaining plungers associated with said syringes in a fixed position when said disposable cartridge is receiving a pressurizing fluid, and a ram which operates a punching needle at a constant speed for punching a hole having a precise diameter in one of said testing channels.

9. The apparatus of claim 8 wherein said test stand further comprises a second heater for maintaining said first and second testing channels at a constant temperature.

10. The apparatus of claim 9 further comprising an optical sensor support for maintaining an optical sensor positioned with respect to a bleeding chamber in one of said testing channels.

11. The apparatus of claim 9, wherein said test stand further provides a connection between a bleeding chamber centrally positioned with respect to said channel hole and a source of saline solution.

12. The apparatus of claim 8, wherein said test stand includes a source of pressurizing fluid coupled to said fluidic coupling inlets when said cartridge is received in said test stand.

13. The apparatus of claim 12, wherein said test stand includes first and second pressure transducers which measure the blood pressure in said first and second testing chambers.

14. A disposable cartridge for measuring physical properties of blood comprising:

a water compartment supporting a platform, said platform having at least one fluidic coupling, and having a guide for positioning at least one syringe holding a blood sample into said fluidic coupling which forms a sealed assembly therewith;

at least one testing station located on said platform for subjecting blood flowing from said syringe to a test condition, and connected to discharge tested blood in said waste compartment; and, conduit means connecting said at least one syringe to said test station.

15. A disposable cartridge according to claim 14, wherein said testing station comprises means for creating a precise opening in said conduit means to simulate bleeding.

16. A disposable cartridge according to claim 14 further comprising a second syringe having a blood sample forming a sealed assembly with said cartridge and a second testing station which includes a flow channel connected to said second syringe having a blood sample which includes a blood platelet activating substance.

17. The disposable apparatus of claim 14 further comprising a conduit extending through said fluidic coupling along an axis of said syringe, and connected to receive a pressurizing media.

18. The disposable cartridge of claim 14, wherein said test station further comprises a columnar pressure chamber having a volume of fluid immiscible with blood which is displaced by said blood, and which is connectable to a pressure transducer for monitoring pressure resulting from blood flowing into said columnar pressure chamber.

19. The disposable cartridge of claim 14 wherein said testing station includes means for introducing a shear force to blood flowing in said channel, thereby activating blood platelets.

* * * * *

UNITED STATES PATENT AND TRADEMARK OFFICE
CERTIFICATE OF CORRECTION

PATENT NO. : 5,316,730
DATED : May 31, 1994
INVENTOR(S) : Blake et al

It is certified that error appears in the above-identified patent and that said Letters Patent is hereby corrected as shown below:

Column 8:

In claim 1, line 50, change "displaying" to --displacing--.

Column 9:

In claim 7, line 5, after "1," insert --wherein--.

Column 10:

In claim 14, line 9, change "water" to --waste--;

line 19, change "test" to --testing--.

Signed and Sealed this

Eleventh Day of October, 1994

Attest:

BRUCE LEHMAN

Attesting Officer

Commissioner of Patents and Trademarks